(12) United States Patent
Doi et al.

(10) Patent No.: US 8,025,881 B2
(45) Date of Patent: Sep. 27, 2011

(54) BMP ANTIBODIES AND METHODS OF TREATING KIDNEY DISEASE USING THE SAME

(75) Inventors: Toshio Doi, Kyoto (JP); Hideharu Abe, Tokushima (JP); Naoshi Fukushima, Shizuoka (JP); Hitoshi Tai, Shizuoka (JP); Takakazu Mizuno, Kanagawa (JP); Masahiko Kinosaki, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/374,473

(22) PCT Filed: Jul. 19, 2007

(86) PCT No.: PCT/JP2007/064280
§ 371 (c)(1),
(2), (4) Date: May 21, 2009

(87) PCT Pub. No.: WO2008/010556
PCT Pub. Date: Jan. 24, 2008

(65) Prior Publication Data
US 2010/0003245 A1 Jan. 7, 2010

(30) Foreign Application Priority Data
Jul. 21, 2006 (JP) .................. 2006-199852

(51) Int. Cl.
*A61K 39/395* (2006.01)
*C12N 5/12* (2006.01)
*C07K 16/00* (2006.01)
*C07K 16/18* (2006.01)
*C07K 16/22* (2006.01)

(52) U.S. Cl. .................. 424/145.1; 424/141.1; 435/335; 435/325; 435/346; 530/387.1; 530/388.1; 530/388.24

(58) Field of Classification Search .................. None
See application file for complete search history.

(56) References Cited

U.S. PATENT DOCUMENTS
2008/0025967 A1    1/2008  Doi et al.

FOREIGN PATENT DOCUMENTS

| JP | 2000510835 | 8/2000 |
|---|---|---|
| JP | 2001523264 | 11/2001 |
| JP | 2004520295 | 7/2004 |
| WO | 9741881 | 11/1997 |
| WO | WO9741880 A1 | 11/1997 |
| WO | 9850060 | 11/1998 |
| WO | 0247713 | 6/2002 |
| WO | 0254940 | 7/2002 |
| WO | 2005026344 | 3/2005 |

OTHER PUBLICATIONS

Vukicevic et al., 1996, PNAS USA 93:9021-9026.*
Shen et al.*
Massague, 1987, Cell 49:437-438.*
Abe et al., "Type IV collagen is transcriptionally regulated by Smad1 under advanced glycation end product (AGE) stimulation," J. Biol. Chem., 279:14201-06 (2004).
Bosukonda et al., "Characterization of receptors for osteogenic protein-1/bone morphogenetic protein-7 (OP-1/BMP-7) in rat kidneys," Kidney Int., 58:1902-11 (2000).
Ghosh Choudhury et al., "Bone morphogenetic protein 2 inhibits platelet-derived growth factor-induced c-fos gene transcription and DNA synthesis in mesangial cells. Involvement of mitogen-activated protein kinase," J. Biol. Chem., 274:10897-10902 (1999).
Ghosh Choudhury et al., "Bone morphogenetic protein-2 inhibits MAPK-dependent Elk-1 transactivation and DNA synthesis induced by EGF in mesangial cells," Biochem. Biophys. Res. Commun., 258:490-496 (1999).
Goumans et al., "Balancing the activation state of the endothelium via two distinct TGF-beta type I receptors," EMBO J., 21:1743-53 (2002).
Jiang et al., "Convergence of bone morphogenetic protein and laminin-1 signaling pathways promotes proliferation and colony formation by fetal mouse pancreatic cells," Exp. Cell Res., 308:114-122 (2005).
Koyama et al., "Evidence for the involvement of bone morphogenetic protein-2 in phenytoin-stimulated osteocalcin secretion in human bone cells," Arch. Oral Biol., 45:647-655 (2000).
Langenfeld et al., "The mature bone morphogenetic protein-2 is aberrantly expressed in non-small cell lung carcinomas and stimulates tumor growth of A549 cells," Carcinogenesis., 24:1445-54 (2003).
Li et al., "Role of TGF-beta signaling in extracellular matrix production under high glucose conditions," Kidney Int., 63:2010-19 (2003).
Masuhara et al., "Use of monoclonal antibody to detect bone morphogenetic protein-4 (BMP-4)," Bone, 16:91-96 (1995).
Matsubara et al., "Expression of Smad1 is directly associated with mesangial matrix expansion in rat diabetic nephropathy," Lab Invest, 86:357-368 (2006).
Miyazaki et al., "Inhibition of endogenous BMP in the glomerulus leads to mesangial matrix expansion," Biochem. Biophys. Res. Commun., 340:681-688. Epub 2005 (2006).

(Continued)

*Primary Examiner* — Elizabeth C Kemmerer
(74) *Attorney, Agent, or Firm* — Fish & Richardson P.C.

(57) ABSTRACT

When an anti-human BMP antibody was added to cells of an immortalized human mesangial cell line cultured in the presence of human BMP, the anti-human BMP antibody significantly suppressed the production of type IV collagen in mesangial cells. A number of signaling pathways are involved in abnormal proliferation of type IV collagen. It was therefore completely unpredictable whether merely blocking the BMP signal would indeed suppress the abnormal proliferation of type IV collagen. However, for the first time, the present inventors demonstrated that anti-BMP antibodies are very effective in suppressing the abnormal proliferation of type IV collagen. Thus, anti-BMP antibodies can be used as novel therapeutic agents for kidney diseases associated with abnormal proliferation of the mesangial matrix.

14 Claims, 2 Drawing Sheets

OTHER PUBLICATIONS

Nakagawa et al., "An immuno-light- and electron-microscopic study of the expression of bone morphogenetic protein-2 during the process of ectopic bone formation in the rat," Arch. Oral. Biol., 46:403-411 (2001).

Yanagita et al., "Uterine sensitization-associated gene-1 (USAG-1), a novel BMP antagonist expressed in the kidney, accelerates tubular injury," J. Clin. Invest., 116:70-79. Epub 2005 (2006).

Yanagita, "Modulator of bone morphogenetic protein activity in the progression of kidney diseases," Kidney Int., 70:989-993 (2006).

Zwijsen et al., "New intracellular components of bone morphogenetic protein/Smad signaling cascades," FEBS Lett., 546:133-139 (2003).

European Search Report for App. Ser. No. EP 07 79 1033, dated Jul. 27, 2010, 3 pages.

International Search Report for App. Ser. No. PCT/JP2007/064280, mailed Oct. 9, 2007, 8 pages.

International Preliminary Report on Patentability for App. Ser. No. PCT/JP2007/064280, dated Jan. 27, 2009, 9 pages.

Miyazono et al., "Bone morphogenetic protein receptors and signal transduction," J. Biochem., 147(1):35-51 (2010) (Epub Sep. 17, 2009).

R&D Systems Tools for Cell Biology Research. Human BMP-2/BMP-4 Antibody, Catalog No. MAB3552. Rev. Sep. 24, 2010, 1 page.

Gilboa et al., "Bone Morphogenetic Protein Receptor Complexes on the Surface of Live Cells: A New Oligomerization Mode for Serine/Threonine Kinase Receptors," Mol. Biol. Cell., 11:1023-35 (2000).

Ten Dijke et al., "Identification of Type I Receptors for Osteogenic Protein-1 and Bone Morphogenetic Protein-4," J. Biol. Chem., 269(25):16985-88 (1994).

* cited by examiner

SEQUENCE LISTING

```
<160> NUMBER OF SEQ ID NOS: 29

<210> SEQ ID NO 1
<211> LENGTH: 396
<212> TYPE: PRT
<213> ORGANISM: Homo sapiens

<400> SEQUENCE: 1

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160
```

Leu Gly Asn Asn Ser Ser Phe His His Arg Ile Asn Ile Tyr Glu Ile
            165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
            245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
            290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
            325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
            370                 375                 380

Tyr Gln Asp Met Val Val Glu Gly Cys Gly Cys Arg
385                 390                 395

<210> SEQ ID NO 2
<211> LENGTH: 408
<212> TYPE: PRT
<213> ORGANISM: Homo sapiens

<400> SEQUENCE: 2

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
            85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
            130                 135                 140

```
Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 3
<211> LENGTH: 5243
<212> TYPE: DNA
<213> ORGANISM: Simian virus 40

<400> SEQUENCE: 3
gcctcggcct ctgcataaat aaaaaaaatt agtcagccat ggggcggaga atgggcggaa      60
ctgggcggag ttaggggcgg gatgggcgga gttaggggcg ggactatggt tgctgactaa     120
ttgagatgca tgctttgcat acttctgcct gctgggagc ctgggaactt ccacacctg      180 gttgctgact aattgagatg catgctttgc atacttctgc ctgctgggga gcctggggac     240
tttccacacc ctaactgaca cacattccac agctggttct ttccgcctca gaaggtacct     300
aaccaagttc ctctttcaga ggttatttca ggccatggtg ctgcgccggc tgtcacgcca     360
ggcctccgtt aaggttcgta ggtcatggac tgaaagtaaa aaaacagctc aacgcctttt     420
tgtgtttgtt ttagagcttt tgctgcaatt ttgtgaaggg aagatactg ttgacgggaa     480 acgcaaaaaa ccagaaaggt taactgaaaa accagaaagt taactggtaa gtttagtctt     540
tttgtctttt atttcaggtc catgggtgct gctttaacac tgttggggga cctaattgct     600
```

```
actgtgtctg aagctgctgc tgctactgga ttttcagtag ctgaaattgc tgctggagag   660
gccgctgctg caattgaagt gcaacttgca tctgttgcta ctgttgaagg cctaacaacc   720
tctgaggcaa ttgctgctat aggcctcact ccacaggcct atgctgtgat atctggggct   780
cctgctgcta tagctggatt tgcagcttta ctgcaaactg tgactggtgt gagcgctgtt   840
gctcaagtgg ggtatagatt ttttagtgac tgggatcaca aagtttctac tgttggttta   900
tatcaacaac caggaatggc tgtagatttg tataggccag atgattacta tgatatttta   960
tttcctggag tacaaacctt tgttcacagt gttcagtatc ttgacccag acattggggt  1020 ccaacacttt ttaatgccat ttctcaagct ttttggcgtg taatacaaaa tgacattcct  1080
aggctcacct cacaggagct tgaaagaaga acccaaagat atttaaggga cagtttggca  1140 aggttttag aggaaactac ttggacagta attaatgctc ctgttaattg gtataactct  1200
ttacaagatt actactctac tttgtctccc attaggccta caatggtgag acaagtagcc  1260
aacagggaag ggttgcaaat atcatttggg cacacctatg ataatattga tgaagcagac  1320
agtattcagc aagtaactga gaggtgggaa gctcaaagcc aaagtcctaa tgtgcagtca  1380
ggtgaattta ttgaaaaatt tgaggctcct ggtggtgcaa atcaaagaac tgctcctcag  1440
tggatgttgc ctttacttct aggcctgtac ggaagtgtta cttctgctct aaaagcttat  1500
gaagatggcc ccaacaaaaa gaaaggaag ttgtccaggg gcagctccca aaaaaccaaa  1560
ggaaccagtg caagtgccaa agctcgtcat aaaaggagga atagaagttc taggagttaa  1620
aactggagta gacagcttca ctgaggtgga gtgcttttta aatcctcaaa tgggcaatcc  1680
tgatgaacat caaaaaggct taagtaaaag cttagcagct gaaaaacagt ttacagatga  1740
ctctccagac aaagaacaac tgccttgcta cagtgtggct agaattcctt tgcctaattt  1800
aaatgaggac ttaacctgtg gaaatatttt gatgtgggaa gctgttactg ttaaaactga  1860
ggttattggg gtaactgcta tgttaaactt gcattcaggg acacaaaaaa ctcatgaaaa  1920
tggtgctgga aaacccattc aagggtcaaa ttttcatttt tttgctgttg gtggggaacc  1980
tttggagctg cagggtgtgt tagcaaacta caggaccaaa tatcctgctc aaactgtaac  2040
cccaaaaaat gctacagttg acagtcagca gatgaacact gaccacaagg ctgttttgga  2100
taaggataat gcttatccag tggagtgctg ggttcctgat ccaagtaaaa atgaaaacac  2160
tagatatttt ggaacctaca caggtgggga aaatgtgcct cctgttttgc acattactaa  2220
cacagcaacc acagtgcttc ttgatgagca gggtgttggg cccttgtgca agctgacag  2280 cttgtatgtt tctgctgttg acatttgtgg gctgtttacc aacacttctg gaacacagca  2340
gtggaaggga cttcccagat attttaaaat taccccttaga aagcggtctg tgaaaaaccc  2400
ctacccaatt tcctttttgt taagtgacct aattaacagg aggacacaga gggtggatgg  2460
gcagcctatg attggaatgt cctctcaagt agaggaggtt agggtttatg aggacacaga  2520
ggagcttcct ggggatccag acatgataag atacattgat gagtttggac aaaccacaac  2580
tagaatgcag tgaaaaaaat gctttatttg tgaaatttgt gatgctattg ctttatttgt  2640
aaccattata agctgcaata acaagttaa caacaacaat tgcattcatt ttatgtttca  2700
ggttcagggg gaggtgtggg aggttttta aagcaagtaa aacctctaca aatgtggtat  2760
ggctgattat gatcatgaac agactgtgag gactgagggg cctgaaatga gccttgggac  2820
tgtgaatcaa tgcctgtttc atgccctgag tcttccatgt tcttctcccc accatcttca  2880
tttttatcag catttttcctg gctgtcttca tcatcatcat cactgtttct tagccaatct  2940
aaaactccaa ttcccatagc cacattaaac ttcattttt gatacactga caaactaaac  3000
```

```
tctttgtcca atctctcttt ccactccaca attctgctct gaatactttg agcaaactca    3060
gccacaggtc tgtaccaaat taacataaga agcaaagcaa tgccactttg aattattctc    3120
ttttctaaca aaaactcact gcgttccagg caatgcttta aataatcttt gggcctaaaa    3180
tctatttgtt ttacaaatct ggcctgcagt gttttaggca cactgtactc attcatggtg    3240
actattccag ggggaaatat ttgagttctt ttatttaggt gtttcttttc taagtttacc    3300
ttaacactgc catccaaata atcccttaaa ttgtccaggt tattaattcc ctgacctgaa    3360
ggcaaatctc tggactcccc tccagtgccc tttacatcct caaaaactac taaaaactgg    3420
tcaatagcta ctcctagctc aaagttcagc ctgtccaagg gcaaattaac atttaaagct    3480
ttccccccac ataattcaag caaagcagct gctaatgtag ttttaccact atcaattggt    3540
cctttaaaca gccagtatct tttttagga atgttgtaca ccatgcattt taaaaagtca    3600
tacaccactg aatccatttt gggcaacaaa cagtgtagcc aagcaactcc agccatccat    3660
tcttctatgt cagcagagcc tgtagaacca aacattatat ccatcctatc caaaagatca    3720
ttaaatctgt ttgttaacat ttgttctcta gttaattgta ggctatcaac ccgcttttta    3780
gctaaaacag tatcaacagc ctgttggcat atggtttttt ggttttgct gtcagcaaat    3840
atagcagcat ttgcataatg cttttcatgg tacttatagt ggctgggctg ttcttttta    3900
atacatttta aacacatttc aaaactgtac tgaaattcca agtacatccc aagcaataac    3960
aacacatcat cacattttgt ttccattgca tactctgtta caagcttcca ggacacttgt    4020
ttagtttcct ctgcttcttc tggattaaaa tcatgctcct ttaacccacc tggcaaactt    4080
tcctcaataa cagaaaatgg atctctagtc aaggcactat acatcaaata ttccttatta    4140
accccttttac aaattaaaaa gctaaaggta cacaattttt gagcatagtt attaatagca    4200
gacactctat gcctgtgtgg agtaagaaaa acagtatgt tatgattata actgttatgc    4260
ctacttataa aggttacaga atattttttcc ataattttct tgtatagcag tgcagctttt    4320
tcctttgtgg tgtaaatagc aaagcaagca agagttctat tactaaacac agcatgactc    4380
aaaaaactta gcaattctga aggaaagtcc ttggggtctt ctaccttct cttctttttt    4440
ggaggagtag aatgttgaga gtcagcagta gcctcatcat cactagatgg catttcttct    4500
gagcaaaaca ggttttcctc attaaaggca ttccaccact gctcccattc atcagttcca    4560
taggttggaa tctaaaatac acaaacaatt agaatcagta gtttaacaca ttatacactt    4620
aaaaatttta tatttacctt agagctttaa atctctgtag gtagtttgtc caattatgtc    4680
acaccacaga agtaaggttc cttcacaaag atcaagtcca aaccacattc taaagcaatc    4740
gaagcagtag caatcaaccc acacaagtgg atctttcctg tataattttc tattttcatg    4800
cttcatcctc agtaagcaca gcaagcatat gcagttagca gacattttct ttgcacactc    4860
aggccattgt ttgcagtaca ttgcatcaac accaggattt aaggaagaag caaatacctc    4920
agttgcatcc cagaagcctc caaagtcagg ttgatgagca tattttactc catcttccat    4980
tttcttgtac agagtattca ttttcttcat tttttcttca tctcctcctt tatcaggatg    5040
aaactccttg cattttttta aatatgcctt tctcatcaga ggaatattcc cccaggcact    5100
cctttcaaga cctagaaggt ccattagctg caaagattcc tctctgttta aaactttatc    5160
catctttgca aagcttttg caaaagccta ggcctccaaa aaagcctcct cactacttct    5220
ggaatagctc agaggccgag gcg                                           5243
```

<210> SEQ ID NO 4  
<211> LENGTH: 33  
<212> TYPE: DNA

```
<213> ORGANISM: Artificial
<220> FEATURE:
<223> OTHER INFORMATION: An artificially synthesized primer sequence

<400> SEQUENCE: 4
caccatggat aaagttttaa acagagagga atc                                    33

<210> SEQ ID NO 5
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 5
ttatgtttca ggttcagggg gaggtgtg                                          28

<210> SEQ ID NO 6
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 6
aagcgggttg atagcctaca                                                   20

<210> SEQ ID NO 7
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 7
attcaagcaa aacagctgct aatg                                              24

<210> SEQ ID NO 8
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 8
cattagcagc tgttttgctt gaat                                              24

<210> SEQ ID NO 9
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 9
ttacaaatct ggcctgcagt                                                   20

<210> SEQ ID NO 10
<211> LENGTH: 4015
<212> TYPE: DNA
<213> ORGANISM: Homo sapiens

<400> SEQUENCE: 10
gcagcgctgc gtcctgctgc gcacgtggga agccctggcc ccggccaccc ccgcgatgcc       60
gcgcgctccc cgctgccgag ccgtgcgctc cctgctgcgc agccactacc gcgaggtgct      120
```

-continued

```
gccgctggcc acgttcgtgc ggcgcctggg gccccagggc tggcggctgg tgcagcgcgg    180
ggacccggcg gctttccgcg cgctggtggc ccagtgcctg gtgtgcgtgc cctgggacgc    240
acggccgccc cccgccgccc cctccttccg ccaggtgtcc tgcctgaagg agctggtggc    300
ccgagtgctg cagaggctgt gcgagcgcgg cgcgaagaac gtgctggcct tcggcttcgc    360
gctgctggac ggggcccgcg ggggcccccc cgaggccttc accaccagcg tgcgcagcta    420
cctgcccaac acggtgaccg acgcactgcg ggggagcggg gcgtggggc tgctgctgcg    480
ccgcgtgggc gacgacgtgc tggttcacct gctggcacgc tgcgcgctct ttgtgctggt    540
ggctcccagc tgcgcctacc aggtgtgcgg ccgccgctg taccagctcg cgctgccac    600
tcaggcccgg cccccgccac acgctagtgg accccgaagg cgtctgggat gcgaacgggc    660
ctggaaccat agcgtcaggg aggccggggt cccctgggc ctgccagccc cgggtgcgag    720
gaggcgcggg ggcagtgcca ccgaagtct gccgttgccc aagaggccca ggcgtggcgc    780
tgccctgag ccggagcgga cgcccgttgg gcaggggtcc tgggcccacc cgggcaggac    840
gcgtggaccg agtgaccgtg gtttctgtgt ggtgtcacct gccagacccg ccgaagaagc    900
cacctctttg gagggtgcgc tctctggcac gcgccactcc cacccatccg tgggccgcca    960
gcaccacgcg ggccccccat ccacatcgcg gccaccacgt cctgggaca cgccttgtcc   1020
cccggtgtac gccgagacca agcacttcct ctactcctca ggcgacaagg agcagctgcg   1080
gccctccttc ctactcagct ctctgaggcc cagcctgact ggcgctcgga ggctcgtgga   1140
gaccatcttt ctgggttcca ggccctggat gccaggact ccccgcaggt tgccccgcct   1200
gccccagcgc tactggcaaa tgcggcccct gtttctggag ctgcttggga accacgcgca   1260
gtgcccctac ggggtgctcc tcaagacgca ctgcccgctg cgagctgcgg tcaccccagc   1320
agccggtgtc tgtgcccggg agaagcccca gggtctgtg gcggccccg aggaggagga   1380
cacagacccc cgtcgcctgg tgcagctgct ccgccagcac agcagcccct ggcaggtgta   1440
cggcttcgtg cgggcctgcc tgcgccggct ggtgcccca ggcctctggg gctccaggca   1500
caacgaacgc cgcttcctca ggaacaccaa gaagttcatc tccctgggga agcatgccaa   1560
gctctcgctg caggagctga cgtggaagat gagcgtgcgg gactgcgctt ggctgcgcag   1620
gagcccaggg gttggctgtg ttccggccgc agagcaccgt ctgcgtgagg agatcctggc   1680
caagttcctg cactggctga tgagtgtgta cgtcgtcgag ctgctcaggt ctttctttta   1740
tgtcacggag accacgtttc aaaagaacag gctctttttc taccggaaga gtgtctggag   1800
caagttgcaa agcattggaa tcagacagca cttgaagagg gtgcagctgc gggagctgtc   1860
ggaagcagag gtcaggcagc atcgggaagc caggcccgcc ctgctgacgt ccagactccg   1920
cttcatcccc aagcctgacg ggctgcgcc gattgtgaac atggactacg tcgtgggagc   1980
cagaacgttc cgcagagaaa agagggccga gcgtctcacc tcgagggtga aggcactgtt   2040
cagcgtgctc aactacgagc gggcgcgcg ccccggcctc ctgggcgcct ctgtgctggg   2100
cctggacgat atccacaggg cctggcgcac cttcgtgctg cgtgtgcggg cccaggaccc   2160
gccgcctgag ctgtactttg tcaaggtgga tgtgacgggc gcgtacgaca ccatcccca   2220
ggacaggctc acggaggtca tcgccagcat catcaaaccc cagaacacgt actgcgtgcg   2280
tcggtatgcc gtggtccaga aggccgccca tgggcacgtc cgcaaggcct tcaagagcca   2340
cgtctctacc ttgacagacc tccagccgta catgcgacag ttcgtggctc acctgcagga   2400
gaccagcccg ctgagggatg ccgtcgtcat cgagcagagc tcctccctga atgaggccag   2460
cagtggcctc ttcgacgtct tcctacgctt catgtgccac cacgccgtgc gcatcagggg   2520
```

```
caagtcctac gtccagtgcc aggggatccc gcagggctcc atcctctcca cgctgctctg    2580
cagcctgtgc tacggcgaca tggagaacaa gctgtttgcg gggattcggc gggacgggct    2640
gctcctgcgt ttggtggatg atttcttgtt ggtgacacct caccctcaccc acgcgaaaac   2700 cttcctcagg accctggtcc gaggtgtccc tgagtatggc tgcgtggtga acttgcggaa    2760
gacagtggtg aacttccctg tagaagacga ggccctgggt ggcacggctt ttgttcagat    2820
gccggcccac ggcctattcc cctggtgcgg cctgctgctg gatacccgga ccctggaggt    2880
gcagagcgac tactccagct atgcccggac ctccatcaga gccagtctca ccttcaaccg    2940
cggcttcaag gctgggagga acatgcgtcg caaactcttt ggggtcttgc ggctgaagtg    3000
tcacagcctg tttctggatt tgcaggtgaa cagcctccag acggtgtgca ccaacatcta    3060
caagatcctc ctgctgcagg cgtacaggtt tcacgcatgt gtgctgcagc tcccatttca    3120
tcagcaagtt tggaagaacc ccacattttt cctgcgcgtc atctctgaca cggcctccct    3180
ctgctactcc atcctgaaag ccaagaacgc agggatgtcg ctgggggcca agggcgccgc    3240
cggccctctg ccctccgagg ccgtgcagtg gctgtgccac caagcattcc tgctcaagct    3300
gactcgacac cgtgtcacct acgtgccact cctggggtca ctcaggacag cccagacgca    3360
gctgagtcgg aagctcccgg ggacgacgct gactgccctg gaggccgcag ccaacccggc    3420
actgccctca gacttcaaga ccatcctgga ctgatggcca cccgcccaca gccaggccga    3480
gagcagacac cagcagccct gtcacgccgg gctctacgtc ccagggaggg aggggcggcc    3540
cacacccagg cccgcaccgc tgggagtctg aggcctgagt gagtgtttgg ccgaggcctg    3600
catgtccggc tgaaggctga gtgtccggct gaggcctgag cgagtgtcca gccaagggct    3660
gagtgtccag cacacctgcc gtcttcactt ccccacaggc tggcgctcgg ctccacccca    3720
gggccagctt ttcctcacca ggagcccggc ttccactccc cacataggaa tagtccatcc    3780
ccagattcgc cattgttcac ccctcgccct gccctccttt gccttccacc cccaccatcc    3840
aggtggagac cctgagaagg accctgggag ctctgggaat ttggagtgac caaaggtgtg    3900
ccctgtacac aggcgaggac cctgcacctg gatgggggtc cctgtgggtc aaattggggg    3960
gaggtgctgt gggagtaaaa tactgaatat atgagttttt cagttttgaa aaaaa         4015
```

<210> SEQ ID NO 11
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 11
tgacagggct gctggtgtct g                                              21

<210> SEQ ID NO 12
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 12
caccatgccg cgcgctcccc gctgccga                                       28

<210> SEQ ID NO 13
<211> LENGTH: 24
<212> TYPE: DNA
<213> ORGANISM: Artificial
<220> FEATURE:

<223> OTHER INFORMATION: An artificially synthesized primer sequence

<400> SEQUENCE: 13
gccttctgga ccacggcata ccga                                          24

<210> SEQ ID NO 14
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 14
caccggcact gttcagcgtg ctcaactacg ag                                 32

<210> SEQ ID NO 15
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 15
tcagtccagg atggtcttga agtc                                          24

<210> SEQ ID NO 16
<211> LENGTH: 4
<212> TYPE: PRT
<213> ORGANISM: Artificial
<220> FEATURE:
<223> OTHER INFORMATION: An artificially synthesized linker sequence

<400> SEQUENCE: 16

Gly Gly Gly Ser
1

<210> SEQ ID NO 17
<211> LENGTH: 4
<212> TYPE: PRT
<213> ORGANISM: Artificial
<220> FEATURE:
<223> OTHER INFORMATION: An artificially synthesized linker sequence

<400> SEQUENCE: 17

Ser Gly Gly Gly
1

<210> SEQ ID NO 18
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 18

Gly Gly Gly Gly Ser
1               5

<210> SEQ ID NO 19
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 19

Ser Gly Gly Gly Gly

```
1               5

<210> SEQ ID NO 20
<211> LENGTH: 6
<212> TYPE: PRT
<213> ORGANISM: Artificial
<220> FEATURE:
<223> OTHER INFORMATION: An artificially synthesized linker sequence

<400> SEQUENCE: 20

Gly Gly Gly Gly Gly Ser
1               5

<210> SEQ ID NO 21
<211> LENGTH: 6
<212> TYPE: PRT
<213> ORGANISM: Artificial
<220> FEATURE:
<223> OTHER INFORMATION: An artificially synthesized linker sequence

<400> SEQUENCE: 21

Ser Gly Gly Gly Gly Gly
1               5

<210> SEQ ID NO 22
<211> LENGTH: 7
<212> TYPE: PRT
<213> ORGANISM: Artificial
<220> FEATURE:
<223> OTHER INFORMATION: An artificially synthesized linker sequence

<400> SEQUENCE: 22

Gly Gly Gly Gly Gly Gly Ser
1               5

<210> SEQ ID NO 23
<211> LENGTH: 7
<212> TYPE: PRT
<213> ORGANISM: Artificial
<220> FEATURE:
<223> OTHER INFORMATION: An artificially synthesized linker sequence

<400> SEQUENCE: 23

Ser Gly Gly Gly Gly Gly Gly
1               5

<210> SEQ ID NO 24
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 24

Gly Gly Gly Gly Ser
1               5

<210> SEQ ID NO 25
<211> LENGTH: 5
<212> TYPE: PRT
<213> ORGANISM: Artificial
<220> FEATURE:
<223> OTHER INFORMATION: An artificially synthesized linker sequence

<400> SEQUENCE: 25

Ser Gly Gly Gly Gly
1               5
```

```
<210> SEQ ID NO 26
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 26
gggatcccca gtcccaagca tcacccacag                                     30

<210> SEQ ID NO 27
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 27
ctcgagttag ttcttattct tcttcctgga                                     30

<210> SEQ ID NO 28
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 28
gggatccccc aagccaaaca caaacagcgg                                     30

<210> SEQ ID NO 29
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 29
ctcgagttag ctggacttaa ggcgtttccg                                     30
```

BMP ANTIBODIES AND METHODS OF TREATING KIDNEY DISEASE USING THE SAME

CROSS-REFERENCE TO RELATED APPLICATIONS

This application is the National Stage of International Application Serial No. PCT/JP2007/064280, filed on Jul. 19, 2007, which claims the benefit of Japanese Application Serial No. 2006-199852, filed on Jul. 21, 2006.

TECHNICAL FIELD

The present invention relates to novel agents for preventing and/or treating kidney diseases.

BACKGROUND ART

Kidney diseases are defined as diseases associated with primary or secondary renal disorders and are treated by diet therapy, therapeutic exercises, or pharmaceutical agents. Dialysis treatment or kidney transplantation may be needed as symptoms advance. Thus, there is a demand for more effective therapeutic agents.

Pathological features of progressive glomerular disorders include the growth of mesangial cells and glomerulosclerosis. Thickening of the glomerular basement membrane and mild increase in glomerular size are observed at the early stage of diabetic nephropathy. Diffuse expansion of mesangial matrix is observed several years after onset. This phenomenon is assumed to be caused by an abnormal increase of extracellular matrix proteins such as type IV and I collagens, fibronectin, and laminin. Abnormal remodeling of the matrix is also found in glomerular mesangial cells in kidney diseases such as IgA nephropathy or Alport's syndrome, and is known to eventually lead to glomerulosclerosis. Thus, the abnormal increase of mesangial matrix is closely involved in diseases associated with glomerulosclerosis.

In diabetic nephropathy, the mechanism underlying the overproduction of type IV collagen, which is a mesangial matrix protein, has been reported to have a number of pathways. Various molecules are assumed to be involved in the overproduction. Transforming growth factor-β (TGF-β) activates Smad2 and Smad3 via activin receptor-like kinase 5 (ALK5), a type I receptor, resulting in overproduction of extracellular matrix proteins such as α1 type IV collagen (Non-Patent Document 1). Smad1 has been demonstrated to be directly involved in the overproduction of type IV collagen (Patent Document 1). Smad1 is known to be a member of the bone morphogenetic protein (BMP) signaling system. BMP activates Smad1 via the type I receptors ALK2, 3, and 6, thereby regulating the transcription of target genes (Non-Patent Document 2). In addition to Smad1, Smad5 and Smad8 are involved in BMP signaling. Smad1 transduces the TGF-β signal via ALK1 in endothelial cells, hematopoietic cells, and the like, thereby participating in the transcriptional regulation of target genes (Non-Patent Document 3).

Suppressing the overproduction of mesangial matrix proteins is expected to ameliorate kidney diseases including diabetic nephropathy. As described above, however, the mechanism underlying the overproduction of mesangial matrix proteins including type IV collagen is complicated, and to date, it is unknown what pathway made of which combination of members contributes to this overproduction.

Patent Document 1: WO2005/026344
Non-Patent Document 1: Li J. H. et al., Kidney International, (2003) 63, 2010-2019
Non-Patent Document 2: Zwijsen A. et al., FEBS Letters (2003) 546, 133-139
Non-Patent Document 3: Goumans M. J. et al., EMBO J., (Apr. 2, 2002) 21(7), 1743-53

DISCLOSURE OF THE INVENTION

Problems to be Solved by the Invention

The present invention was achieved in view of the above circumstances. An objective of the present invention is to provide novel agents for treating kidney diseases.

Means for Solving the Problems

The present inventors conducted dedicated studies to achieve the objective mentioned above. Among substances involved in abnormal proliferation of the mesangial matrix, the present inventors focused on BMP and investigated the influence of BMP signal blockage on the production of the mesangial matrix. Specifically, the present inventors added an anti-human BMP antibody to cells of an immortalized human mesangial cell line cultured in the presence of human BMP, and then carried out ELISA to determine the amount of type IV collagen, which is a mesangial matrix protein, produced by the cell line. The result showed that the anti-human BMP antibody significantly reduced the amount of type IV collagen produced by the mesangial cells. A number of signaling pathways are involved in the abnormal proliferation of mesangial matrix proteins including type IV collagen. It was therefore completely unpredictable whether blocking merely one of the pathways would indeed suppress the abnormal proliferation of the mesangial matrix. However, the present inventors demonstrated for the first time that blocking BMP signaling using an anti-BMP antibody suppressed the abnormal proliferation of the mesangial matrix very effectively. Thus, anti-BMP antibodies can be used as novel pharmaceutical agents for preventing and treating diseases caused by the abnormal proliferation of the mesangial matrix. The present invention relates to the use of anti-BMP antibodies and specifically provides:

[1] an agent for preventing and/or treating a kidney disease, which comprises as an active ingredient an antibody having BMP-neutralizing activity, or a fragment thereof;
[2] the preventive and/or therapeutic agent of [1], wherein the BMP is a human BMP;
[3] the preventive and/or therapeutic agent of [1] or [2], wherein the BMP is BMP-2 or BMP-4;
[4] the preventive and/or therapeutic agent of any one of [1] to [3], wherein the antibody is a monoclonal antibody;
[5] the preventive and/or therapeutic agent of any one of [1] to [4], wherein the antibody is a recombinant antibody;
[6] the preventive and/or therapeutic agent of [5], wherein the antibody is a chimeric antibody, humanized antibody, or human antibody;
[7] the preventive and/or therapeutic agent of any one of [1] to [6], wherein the kidney disease is selected from the group consisting of: diabetic nephropathy, chronic glomerulonephritis, lupus nephritis, interstitial nephritis, and nephrosclerosis (benign and malignant);
[8] the preventive and/or therapeutic agent of any one of [1] to [4] and [7], wherein the antibody is selected from the group consisting of: an antibody produced by the hybridoma deposited under the accession number FERM ABP-10873, an antibody produced by the hybridoma deposited under the accession number FERM ABP-10874, an antibody produced by the hybridoma deposited under the accession number FERM ABP-10875, and an antibody produced by the hybridoma deposited under the accession number FERM ABP-10876;

[9] a hybridoma deposited under the accession number FERM ABP-10873;

[10] a hybridoma deposited under the accession number FERM ABP-10874;

[11] a hybridoma deposited under the accession number FERM ABP-10875;

[12] a hybridoma deposited under the accession number FERM ABP-10876;

[13] an anti-human BMP-4 antibody produced by the hybridoma of any one of [9] to [12];

[14] a method for preventing and/or treating a kidney disease, which comprises administering an antibody having BMP-neutralizing activity, or a fragment thereof; and

[15] use of an antibody having BMP-neutralizing activity or a fragment thereof in producing a pharmaceutical agent for preventing and/or treating a kidney disease.

BEST MODE FOR CARRYING OUT THE INVENTION

Figure 1:
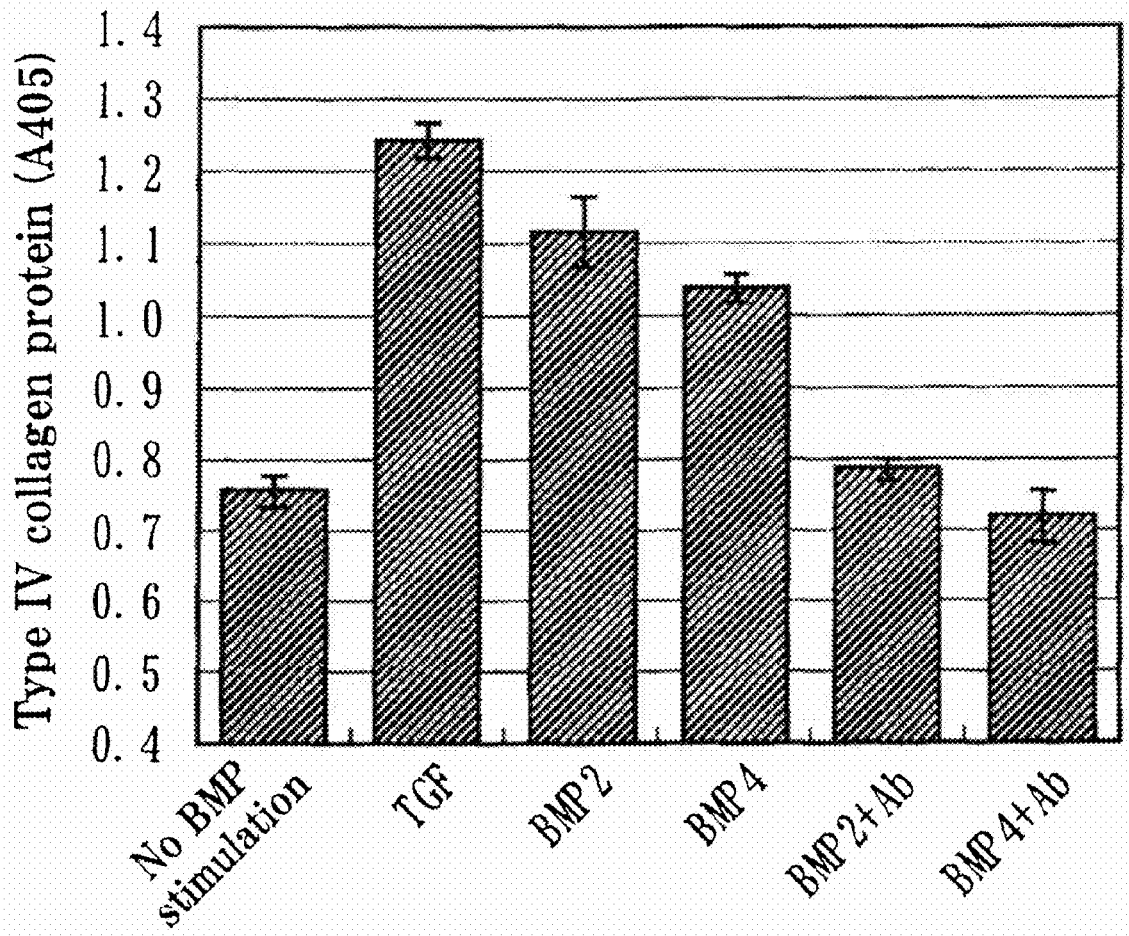
FIG. 1 is a graph showing that an anti-human BMP antibody suppressed the production of type IV collagen in mesangial cells. When an anti-human BMP antibody was added to BMP-2- or BMP-4-stimulated cells of a human mesangial cell line, the production of type IV collagen in the cell line was suppressed to a level comparable to that in the absence of BMP stimulation.

The present invention relates to agents for preventing and/or treating kidney diseases, which contain as an active ingredient an antibody having BMP-neutralizing activity or a fragment thereof. The present inventors discovered that anti-BMP-2/4 antibodies significantly suppressed the production of mesangial matrix in mesangial cells.

BMP is a member of the TGF-β superfamily consisting of TGF-β, activin, inhibin, Müllerian inhibitory factor, and others. BMP was originally identified as a protein that induces bone formation, and then was demonstrated to be involved in the limb development and neural differentiation at developmental stages. Recently, BMP has also been reported to be involved in the regulation of metanephrogenic development. To date, there are about 20 types of reported BMP isoforms. Known BMP family members include BMP-6, BMP-5, BMP-7/OP-1, BMP-8b/OP-3, BMP-8a/OP-3, 60A, DPP, BMP-2, BMP-4, GDF-5/CDMP-1, GDF-6/CDMP-2/BMP-13, GDF-7/CDMP-3/BMP-12, GDF-1, GDF-3, BMP-9, BMP-3, and GDF-10.

Like other TGF-β superfamily members, BMP-2 and BMP-4 are synthesized as precursor proteins. Then, the C-terminal portions containing the conserved seven cysteines are cleaved off, and the resulting glycoproteins with a molecular weight of about 30 kDa take a dimer structure by getting linked together via a disulfide bond. BMP-2 and BMP-4 are structurally more similar than the others in the BMP family.

The sequences of BMP-2 and BMP-4 are known; the sequences of human BMP-2 and BMP-4, and mouse BMP-2 and BMP-4 are disclosed under Accession Nos. M22489, M22490, NM_007553, and NM_007554 in GenBank, respectively. The accession number of rat BMP-4 is NM_012827. The amino acid sequences of rat and mouse BMP-4 are identical to each other. Furthermore, only 2 out of 116 amino acids are different in human and rat BMP-4 at their C termini after cleavage.

BMP transduces signals via the BMP receptor. Type I and type II BMP receptors (BMPRs) that bind to BMP are known. Already reported mammalian BMPRs are: three types of type I receptors, ALK-3 (BMPR-IA), ALK-6 (BMPR-IB), and ALK-2 (ActR-1); and three types of type II receptors, BMPR-II, ActR-II, and ActR-IIB. All of the type I and type II receptors are serine/threonine kinase type receptors having a single transmembrane domain. The type I receptors have a characteristic amino acid sequence containing glycine-serine repeats called GS domains, which are located immediately after the transmembrane domain, while the type II receptors have no GS domains. The BMP signal via the BMP receptor is known to activate Smad and MAPK. Some substances have been reported to suppress the activation of the BMP receptor and thus block BMP signaling by inhibiting the binding between BMP and BMP receptor. Such BMP antagonists include, for example, previously identified noggin, chordin, and follistatin. Furthermore, CAN family members such as DAN, cerberus, sclerostin, and ectodin have been reported to have BMP antagonistic activity.

Every BMP serves as a potential target in the present invention, as long as it can enhance the overexpression of mesangial matrix via BMP receptor. There is no limitation on the type; however, BMP-2 and BMP-4 are preferred. Furthermore, animals from which BMP is derived are not particularly limited. BMP can be derived, for example, from rodents (mice, rats, hamsters, rats, etc.), pigs, bovines, horses, donkeys, goats, dogs, cats, chimpanzees, orangutans, humans, and others. Human BMP is preferred. The amino acid sequences of human BMP-2 and BMP-4 are shown in SEQ ID NOs: 1 and 2, respectively.

Herein, an "antibody having BMP-neutralizing activity" refers to an antibody that blocks intracellular signaling via BMP receptor through binding to BMP and thus causes loss of or suppresses the biological activity of the cells. Such biological activities include, but are not limited to, for example, activities of inducing or suppressing the production of a bioactive substance (for example, chemokines, inflammatory cytokines, and such), activities of enhancing or suppressing the secretion of a bioactive substance, growth activities, growth-inducing activities, survival activities, differentiation activities, differentiation-inducing activities, transcriptional activities, membrane transport activities, binding activities, proteolytic activities, phosphorylation/dephosphorylation activities, oxidation-reduction activities, transfer activities, nucleotlytic activities, dehydration activities, cell death-inducing activities, and apoptosis-inducing activities. "Antibodies having BMP-neutralizing activity" of the present invention may recognize multiple types of BMPs or have the activity of neutralizing multiple types of BMPs, as long as they have the activity of neutralizing any of the BMPs of the present invention. For example, the antibodies may bind to both human and rat BMP-4. The "antibodies having BMP-neutralizing activity" in the present invention may be polyclonal or monoclonal antibodies. In a preferred embodiment, the antibodies are monoclonal antibodies.

Such monoclonal antibodies having BMP-neutralizing activity can be obtained, for example, by the following procedure: anti-BMP monoclonal antibodies are prepared by using as an antigen BMP or a fragment thereof that is derived from a mammal, such as human or mouse, by known methods, and then antibodies having BMP-neutralizing activity are selected from the thus obtained anti-BMP monoclonal antibodies. Specifically, immunization is achieved by conventional immunization methods using as a sensitizing antigen a desired antigen or cells expressing the desired antigen. Anti-BMP monoclonal antibodies can be prepared by fusing the obtained immune cells with known parental cells using conventional cell fusion methods, and screening them for monoclonal antibody-producing cells (hybridomas) by conventional screening methods. Animals to be immunized include, for example, mammals, such as mice, rats, rabbits, sheep, monkeys, goats, donkeys, cows, horses, and pigs. The antigen can be prepared using the known BMP gene sequence according to known methods, for example, by methods using baculovirus (for example, WO 98/46777). Alternatively, anti-BMP monoclonal antibodies can be prepared through selection from those commercially available by detecting BMP-neutralizing activity.

Hybridomas can be prepared, for example, according to the method of Milstein et al. (Kohler, G. and Milstein, C., Methods Enzymol., (1981) 73, 3-46) or such. When the immunogenicity of an antigen is low, immunization may be performed after linking the antigen with a macromolecule having immunogenicity, such as albumin.

In a preferred embodiment, the antibodies of the present invention having BMP-neutralizing activity include monoclonal antibodies having the activity of neutralizing human BMP. As described in the Examples, the present inventors discovered monoclonal antibodies having the activity of neutralizing human BMP. The monoclonal antibodies having the activity of neutralizing human BMP may be commercially available anti-human BMP monoclonal antibodies or antibodies prepared by the methods described above.

Immunogens that are used to prepare monoclonal antibodies having the activity of neutralizing human BMP are not particularly limited, as long as they enable the preparation of antibodies having the activity of neutralizing human BMP. For example, human BMPs are known to include a number of isoforms, and any isoform may be used as the immunogen, or a peptide fragment of human BMP or a human BMP sequence containing artificial mutations may be used as the immunogen, as long as it enables the preparation of antibodies having the activity of neutralizing human BMP. Human BMP-2 and BMP-4 can be preferably used as the immunogen in preparing antibodies of the present invention having BMP-neutralizing activity.

Specifically, such antibodies include, for example, anti-human BMP monoclonal antibodies produced by hybridomas BF1009 and BF1066. As described below, hybridomas BF1009 and BF1066 were prepared by the present inventors from mice administered with human BMP-4. Furthermore, the present inventors demonstrated that the antibodies produced by hybridomas BF1009 and BF1066 showed the effect of ameliorating kidney diseases by reducing the level of excreted urinary albumin in kidney disease model animals. The isotype of monoclonal antibody produced by hybridoma BF1009 is IgG2b for the heavy chain and κ for the light chain. The isotype of monoclonal antibody produced by hybridoma BF1066 is IgG1 for the heavy chain and κ for the light chain.

The hybridoma BF1009 was deposited on Jul. 18, 2007 in the International Patent Organism Depositary, National Institute of Advanced Industrial Science and Technology. Information specifying the deposition is as follows:
(i) Name and Address of Depositary Institution
Name: International Patent Organism Depositary, National Institute of Advanced Industrial Science and Technology
Address: Tsukuba Central 6, 1-1-1 Higashi, Tsukuba, Ibaraki, Japan (Zip code: 305-8566)
(ii) Date of Deposition: Jul. 18, 2007
(iii) Identification reference given by the depositor: $BF_{1009}$-1
(iv) Reception Number: FERM ABP-10873

The hybridoma BF1009 was deposited on Jul. 18, 2007 in the International Patent Organism Depositary, National Institute of Advanced Industrial Science and Technology. Information specifying the deposition is as follows:
(i) Name and Address of Depositary Institution
Name: International Patent Organism Depositary, National Institute of Advanced Industrial Science and Technology
Address: Tsukuba Central 6, 1-1-1 Higashi, Tsukuba, Ibaraki, Japan (Zip code: 305-8566)
(ii) Date of Deposition: Jul. 18, 2007
(iii) Identification reference given by the depositor: BF1009-2
(iv) Reception Number: FERM ABP-10874

The hybridoma BF1066 was deposited on Jul. 18, 2007 in the International Patent Organism Depositary, National Institute of Advanced Industrial Science and Technology. Information specifying the deposition is as follows:
(i) Name and Address of Depositary Institution
Name: International Patent Organism Depositary, National Institute of Advanced Industrial Science and Technology
Address: Tsukuba Central 6, 1-1-1 Higashi, Tsukuba, Ibaraki, Japan (Zip code: 305-8566)
(ii) Date of Deposition: Jul. 18, 2007
(iii) Identification reference given by the depositor: BF1066-1
(iv) Reception Number: FERM ABP-10875

The hybridoma BF1066 was deposited on Jul. 18, 2007 in the International Patent Organism Depositary, National Institute of Advanced Industrial Science and Technology. Information specifying the deposition is as follows:
(i) Name and Address of Depositary Institution
Name: International Patent Organism Depositary, National Institute of Advanced Industrial Science and Technology
Address: Tsukuba Central 6, 1-1-1 Higashi, Tsukuba, Ibaraki, Japan (Zip code: 305-8566)
(ii) Date of Deposition: Jul. 18, 2007
(iii) Identification reference given by the depositor: BF1066-2
(iv) Reception Number: FERM ABP-10876

Herein, the above-described antibodies of the present invention are not particularly limited, as long as they have BMP-neutralizing activity. The antibodies also include recombinant antibodies such as chimeric antibodies, humanized antibodies, and human antibodies. The chimeric antibodies comprise, for example, the heavy and light chain constant regions of a human antibody, and the heavy and light chain variable regions of a non-human mammal, such as mouse. The chimeric antibodies can be produced by known methods. For example, the antibodies can be produced by cloning an antibody gene from hybridomas, inserting it into an appropriate vector, and introducing the construct into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable regions (V regions) are synthesized from mRNA of hybridomas (for example, hybridomas BF1009 and BF1066 of the present invention) using reverse transcriptase. Once DNAs encoding the V regions of an antibody of interest are obtained, these are linked with DNAs encoding the constant regions (C regions) of a desired human antibody. The resulting constructs are inserted into expression vectors. Alternatively, the DNAs encoding the antibody V regions may be inserted into expression vectors comprising DNAs encoding the C regions of a human antibody. The DNAs are inserted into expression vectors so that they are expressed under the regulation of the expression regulatory regions, for example, enhancers and promoters. In the next step, host cells can be transformed with the expression vectors to allow expression of chimeric antibodies.

A humanized antibody, which is also called a reshaped human antibody, is obtained by grafting a complementarity determining region (CDR) of an antibody of a nonhuman mammal such as a mouse, into the CDR of a human antibody. Conventional genetic recombination techniques for the preparation of such antibodies are also known. Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see European Patent Application No. EP 239, 400 and International Patent Application Publication No. WO 96/02576). Human antibody FRs that are ligated via the CDR are selected where the CDR forms a favorable antigen-binding site. As necessary, amino acids in the framework region of an antibody variable region may be substituted such that the CDR of a reshaped human antibody forms an appropriate antigen-binding site (Sato, K. et al., Cancer Res., (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by using a desired antigen to immunize a transgenic animal that comprises an entire repertoire of human antibody genes (see International Patent Application Publication Nos. WO 93/12227, WO 92/03918, WO 94/02602, WO 94/25585, WO 96/34096, and WO 96/33735).

Furthermore, techniques to obtain human antibodies by panning with a human antibody phage library are known. For example, the variable region of a human antibody is expressed as a single chain antibody (scFv) on the surface of a phage, using a phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are well known (see WO 92/01047, WO 92/20791, WO 93/06213, WO 93/11236, WO 93/19172, WO 95/01438, and WO 95/15388).

The amino acid sequence of the heavy chain variable region or light chain variable region may be an amino acid sequence with a substitution, deletion, addition, and/or insertion of one or more amino acids in the amino acid sequence of the heavy chain variable region or light chain variable region of an antibody that has been confirmed to have BMP-neutralizing activity, as long as BMP-neutralizing activity is retained. Methods well known to those skilled in the art to prepare the amino acid sequence of the heavy chain variable region or light chain variable region having BMP-neutralizing activity, which comprises a substitution, deletion, addition, and/or insertion of one or more amino acids in the amino acid sequence of the heavy chain variable region or light chain variable region, include known methods for introducing mutations into proteins. For example, those skilled in the art can prepare mutants functionally equivalent to the heavy chain variable region or light chain variable region of the antibody having BMP-neutralizing activity by introducing appropriate mutations into the amino acids of the heavy chain variable region or light chain variable region of the antibody having BMP-neutralizing activity (for example, antibodies produced by hybridomas BF1009 and BF1066 of the present invention) using site-directed mutagenesis (Hashimoto-Gotoh, T, Mizuno, T, Ogasahara, Y, and Nakagawa, M. An oligodeoxyribonucleotide-directed dual amber method for site-directed mutagenesis. Gene (1995) 152, 271-275; Zoller, M. J., and Smith, M. Oligonucleotide-directed mutagenesis of DNA fragments cloned into M13 vectors. Methods Enzymol. (1983) 100, 468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12, 9441-9456; Kramer W., and Fritz H. J. Oligonucleotide-directed construction of mutations via gapped duplex DNA Methods. Enzymol. (1987) 154, 350-367; Kunkel, T. A. Rapid and efficient site-specific mutagenesis without phenotypic selection. Proc Natl Acad Sci USA. (1985) 82, 488-492) or the like. Thus, heavy chain variable regions or light chain variable regions that comprise mutations at one or more amino acids in the heavy chain variable region or light chain variable region having BMP-neutralizing activity are also included in the heavy chain variable region or light chain variable region of the present invention.

When an amino acid residue is altered, the amino acid is preferably mutated for a different amino acid(s) that conserves the properties of the amino acid side chain. Examples of amino acid side chain properties are: hydrophobic amino acids (A, I, L, M, F, P. W, Y, and V), hydrophilic amino acids (R, D, N, C, E, Q, G, H, K, S, and T), amino acids comprising aliphatic side chains (G, A, V, L, I, and P), amino acids comprising hydroxyl group-containing side chains (S, T, and Y), amino acids comprising sulfur-containing side chains (C and M), amino acids comprising carboxylic acid- and amide-containing side chains (D, N, E, and Q), amino acids comprising basic side chains (R, K, and H), and amino acids comprising aromatic side chains (H, F, Y, and W) (amino acids are represented by one-letter codes in parentheses). Amino acid substitutions within each group are called conservative substitutions. It is already known that a polypeptide comprising a modified amino acid sequence in which one or more amino acid residues in a given amino acid sequence are deleted, added, and/or substituted with other amino acids can retain the original biological activity (Mark, D. F. et al., Proc. Natl. Acad. Sci. USA (1984) 81, 5662-6; Zoller, M. J. and Smith, M., Nucleic Acids Res. (1982) 10, 6487-500; Wang, A. et al., Science (1984) 224, 1431-3; Dalbadie-McFarland, G et al., Proc. Natl. Acad. Sci. USA (1982) 79, 6409-13). Such mutants comprise an amino acid sequence which is at least 70% identical to the amino acid sequence of a heavy chain variable region or light chain variable region of the present invention, more preferably at least 75%, even more preferably at least 80%, still more preferably at least 85%, yet more preferably at least 90%, and most preferably at least 95% identical. Herein, sequence identity is defined as the percentage of residues identical to those in the original amino acid sequence of the heavy chain variable region or light chain variable region, determined after the sequences are aligned and gaps are appropriately introduced to maximize the sequence identity as necessary. The identity of amino acid sequences can be determined by the method described above.

Alternatively, an amino acid sequence of the heavy chain variable region or light chain variable region that comprises a substitution, deletion, addition, and/or insertion of one or more amino acids in the amino acid sequence of the heavy chain variable region or light chain variable region and retains BMP-neutralizing activity can be obtained from nucleic acid that hybridizes under stringent conditions to nucleic acid comprising the nucleotide sequence encoding the amino acid sequence of the heavy chain variable region or light chain variable region. Stringent hybridization conditions to isolate a nucleic acid that hybridizes under stringent conditions to a nucleic acid that comprises the nucleotide sequence encoding the amino acid sequence of the heavy chain variable region or light chain variable region include, for example, the conditions of 6 M urea, 0.4% SDS, 0.5×SSC, and 37° C., or hybridization conditions with stringencies equivalent thereto. With more stringent conditions, for example, the conditions of 6 M urea, 0.4% SDS, 0.1×SSC, and 42° C., isolation of nucleic acids with a much higher homology can be expected. The sequences of the isolated nucleic acids can be determined by the known methods described below. The overall nucleotide sequence homology of the isolated nucleic acid is at least 50% or higher sequence identity, preferably 70% or higher, more preferably 90% or higher (for example, 95%, 96%, 97%, 98%, 99%, or higher).

An amino acid sequence encoded by a nucleic acid that hybridizes under stringent conditions to a nucleic acid comprising the nucleotide sequence encoding the amino acid sequence of the heavy chain variable region or light chain variable region can also be isolated using, instead of the above-described methods using hybridization techniques, gene amplification methods using primers synthesized based on the information of nucleotide sequence encoding the amino acid sequence of the heavy chain variable region or light chain variable region, for example, polymerase chain reaction (PCR).

Specifically, the identity of one nucleotide sequence or amino acid sequence to another can be determined using the algorithm BLAST, by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); www.ncbi.nlm.nih.gov).

Alternatively, the antibodies of the present invention may be minibodies. Such minibodies of the present invention include antibody fragments lacking some portions of a whole antibody (for example, whole IgG), and are not particularly limited as long as they retain BMP-neutralizing activity. The minibodies of the present invention are not particularly limited, as long as they are portions of whole antibodies. The minibodies preferably comprise a heavy chain variable region (VH) or light chain variable region (VL). Particularly preferred minibodies comprise both VH and VL.

The minibodies of the present invention preferably have a smaller molecular weight than whole antibodies. However, the minibodies may form multimers, for example, dimers, trimers, or tetramers, and thus their molecular weights can be greater than those of whole antibodies.

The minibodies of the present invention include, for example, scFv antibodies. ScFv antibodies are single-chain polypeptides constructed by linking a heavy chain variable region ([VH]) and a light chain variable region ([VL]) via a linker or such (Huston, J. S. et al., Proc. Natl. Acad. Sci. U.S.A. (1988) 85, 5879-5883; Plickthun "The Pharmacology of Monoclonal Antibodies" Vol. 113, eds., Resenburg and Moore, Springer Verlag, New York, pp. 269-315, (1994)). The order of the heavy chain variable region and light chain variable region to be linked together is not particularly limited, and they may be arranged in any order. Examples of the arrangements are listed below.

[VH] linker [VL]
[VL] linker [VH]

The amino acid sequence of the heavy chain variable region or light chain variable region may comprise a substitution, deletion, addition, and/or insertion. Furthermore, the heavy chain variable region and light chain variable region may also lack some portions or be added with other polypeptides, as long as they have antigen binding ability when linked together. Alternatively, the variable regions may be chimerized or humanized.

In the present invention, linkers which bind the variable region of the antibody comprise arbitrary peptide linkers that can be introduced using genetic engineering, or synthetic linkers (for example, linkers disclosed in Protein Engineering, (1996) 9(3), 299-305).

The preferred linkers in the present invention are peptide linkers. The lengths of the peptide linkers are not particularly limited and those skilled in the art can appropriately select the lengths depending on the purpose. Typical lengths are 1 to 100 amino acids, preferably 3 to 50 amino acids, more preferably 5 to 30 amino acids, and particularly preferably 12 to 18 amino acids (for example, 15 amino acids).

Amino acid sequences of such peptide linkers include, for example:

```
Ser

Gly·Ser

Gly·Gly·Ser

Ser·Gly·Gly

Gly·Gly·Gly·Ser              (SEQ ID NO: 16)

Ser·Gly·Gly Gly              (SEQ ID NO: 17)

Gly·Gly·Gly·Gly·Ser          (SEQ ID NO: 18)

Ser·Gly·Gly·Gly·Gly          (SEQ ID NO: 19)

Gly·Gly·Gly·Gly·Gly·Ser      (SEQ ID NO: 20)

Ser·Gly·Gly·Gly·Gly·Gly      (SEQ ID NO: 21)

Gly·Gly·Gly·Gly·Gly·Gly·Ser  (SEQ ID NO: 22)

Ser·Gly·Gly·Gly·Gly·Gly·Gly  (SEQ ID NO: 23)
```

```
(Gly·Gly·Gly·Gly·Ser)n        (SEQ ID NO: 24)

(Ser·Gly·Gly·Gly·Gly)n        (SEQ ID NO: 25)
```
where n is an integer of 1 or larger.

Synthetic linkers (chemical crosslinking agents) include crosslinking agents that are routinely used to crosslink peptides, for example, N-hydroxy succinimide (NHS), disuccinimidyl suberate (DSS), bis(succinimidyl) suberate ($BS^3$), dithiobis(succinimidyl propionate) (DSP), dithiobis(succinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis[2-(succinimidoxycarbonyloxy)ethyl]sulfone (sulfo-BSOCOES). These crosslinking agents are commercially available.

Antibodies of the present invention include antibodies in which two or more amino acid residues have been added to the amino acid sequence of an antibody of the present invention. Further, fusion proteins which result from a fusion between one of the above antibodies and a second peptide or protein is included in the present invention. The fusion proteins can be prepared by ligating a polynucleotide encoding an antibody of the present invention and a polynucleotide encoding a second peptide or polypeptide in frame, inserting this into an expression vector, and expressing the fusion construct in a host. Some techniques known to those skilled in the art are available for this purpose. The partner peptide or polypeptide to be fused with an antibody of the present invention may be a known peptide, for example, FLAG (Hopp, T. P. et al., BioTechnology (1988) 6, 1204-1210), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, Protein C fragment. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

The antibodies of the present invention may differ in amino acid sequence, molecular weight, isoelectric point, presence/absence of sugar chains, and conformation depending on the cell or host producing the antibody, or purification method. However, a resulting antibody is included in the present invention, as long as it is functionally equivalent to an antibody of the present invention. For example, when an antibody of the present invention is expressed in prokaryotic cells, for example *Escherichia coli* (*E. coli*), a methionine residue is added to the N terminus of the original antibody amino acid sequence. Such antibodies are included in the present invention.

The scFv of the present invention can be prepared by methods known to those skilled in the art. The scFv can be prepared, for example, by genetic recombination techniques known to those skilled in the art based on the sequence of an antibody that recognizes BMP. Specifically, such scFv can be prepared by constructing a polynucleotide encoding an antibody based on the sequence of an antibody that recognizes BMP, inserting the construct into an expression vector, and then expressing it in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in *E. coli* such as JM109, DH5α, HB101, and XL1-Blue, the expression vectors not only have the above-described characteristics that allow vector amplification in *E. coli*, but must also carry a promoter that allows efficient expression in *E. coli*, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vectors include pGEX-5X-1 (Pharmacia), "QIAexpress system" (Quiagen), pEGFP, or pET (in this case, the host is preferably BL21 that expresses T7 RNA polymerase) in addition to the vectors described above.

The vectors may comprise signal sequences for antibody secretion. As a signal sequence for antibody secretion, a pelB signal sequence (Lei, S. P. et al J. Bacteriol. (1987) 169, 4379) may be used when a protein is secreted into the *E. coli* periplasm. The vector can be introduced into host cells by calcium chloride or electroporation methods, for example.

In addition to vectors for *E. coli*, the vectors for producing the antibodies of the present invention include mammalian expression vectors (for example, pcDNA3 (Invitrogen), pEF-BOS (Nucleic Acids. Res. (1990) 18(17), p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, PHSV, pMV, and pAdexLcw), retroviral expression vectors (for example, pZIPneo), yeast expression vectors (for example, "*Pichia* Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277, 108), MMLV-LTR promoter, EF1α promoter (Mizushima et al., Nucleic Acids Res. (1990) 18, 5322), and CMV promoter, and more preferably they have a gene for selecting transformed cells (for example, a drug resistance gene that allows evaluation using an agent (neomycin, G418, or such). Vectors with such characteristics include pMAM, pDR2, PBK-RSV, PBK-CMV, POPRSV, and pOP13, for example.

In addition, the following method can be used for stable gene expression and gene amplification in cells: CHO cells deficient in a nucleic acid synthesis pathway are introduced with a vector (for example, PCHOI) that carries a DHFR gene which compensates for the deficiency, and the vector is amplified using methotrexate (MTX). Alternatively, the following method can be used for transient gene expression: COS cells with a gene expressing SV40 T antigen on their chromosome are transformed with a vector (pcD and such) with an SV40 replication origin. Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Desired antibodies obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose F. F. (Pharmacia). The present invention comprises antibodies that are highly purified using these purification methods.

The present invention also provides agents for preventing or treating kidney diseases, which comprise as active ingredients fragments and/or modification products of an antibody of the present invention. The fragments and/or modification products of antibodies of the present invention include antibody fragments lacking some portions of the antibodies of the present invention (whole antibodies (for example, whole IgG), recombinant antibodies (for example, chimeric antibodies, humanized antibodies, and human antibodies), and minibodies (for example, scFv antibodies)), and are not particularly limited as long as they retain the ability to bind to their antigens. The antibody fragments of the present invention are not particularly limited, as long as they are portions of whole antibodies. The fragments preferably comprise a heavy chain variable region (VH) and/or a light chain variable region (VL). The amino acid sequence of the VH or VL may comprise substitutions, deletions, additions, and/or insertions. The VH and/or VL may lack some portions, as long as the ability to bind to the antigen is retained. Furthermore, the variable region may be chimerized or humanized. Specifically, antibody fragments include, for example, Fab, Fab', F(ab')2, and Fv. Such antibody fragments can be obtained by constructing genes encoding the antibody fragments, introducing them into expression vectors, and then expressing them in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Furthermore, the antibodies of the present invention may be conjugated antibodies which are linked to any of various molecules, such as polyethylene glycol (PEG), radioactive substances, fluorescent substances, luminescent substances, enzymes, and toxins. Such conjugated antibodies can be obtained by chemically modifying the obtained antibodies. Methods for modifying antibodies have been established in this field (for example, U.S. Pat. No. 5,057,313 and U.S. Pat. No. 5,156,840). The "antibodies" of the present invention also include such conjugated antibodies.

The antibody's activity of binding to BMP can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity.

Antibodies of the present invention having BMP-neutralizing activity can be prepared by selecting antibodies having BMP-neutralizing activity from anti-BMP antibodies prepared as described above. Antibodies having BMP-neutralizing activity can be selected, for example, by the methods described below in Examples. Whether a candidate antibody has BMP-neutralizing activity can be assessed by determining the amount of type IV collagen produced by mesangial cells or cell lines after adding the candidate antibody. When an antibody reduces the amount of type IV collagen produced by the mesangial cells or cell lines in this assay method, the antibody is expected to have BMP-neutralizing activity.

Immortalized human mesangial cell lines can be prepared, for example, by the following procedure.

Human Mesangial Cell Culture

Primary human mesangial cells (MCs) (available from Cambrex (Walkersville, Md.)) are cultured in MsGM growth medium (Cambrex) at 37° C. under an atmosphere of 95% air and 5% carbon dioxide gas.

Preparation of Recombinant Lentivirus

293FT cells are obtained from Invitrogen (Carlsbad, Calif.) and cultured in Dulbecco's modified Eagle's medium (hereinafter abbreviated as "DMEM") supplemented with 10% fetal bovine serum (HyClone, Logan, Utah; hereinafter abbreviated as "FBS"), 1% non-essential amino acid solution, and 1% penicillin-streptomycin solution (100 U/ml and 100 μg/ml, respectively). Unless otherwise stated, all cell culture products are available from Invitrogen (Grand Island, N.Y.).

Recombinant lentivirus can be prepared using ViraPower Lentiviral Expression System (Invitrogen, Carlsbad, Calif.) according to the instruction manual of the manufacturer. The complete SV40T antigen (SV40 TAg; nucleotide No. 2691-5163 of Genbank NC_001669, SEQ ID NO: 3) is prepared from genomic DNA of 293FT cells by PCR amplification using sense and antisense primers: 5'-CACCATG-GATAAAGTTTTAAACAGAGAGGAATC (SEQ ID NO: 4) and 5'-TTATGTTTCAGGTTCAGGGGGAGGTGTG (SEQ ID NO: 5), respectively. The amplified DNA is inserted into pLenti6/V5-D TOPO vector to construct pLenti6-Tag. A Kozak motif is designed according to the instruction manual. Then, the point mutation tsA58 is introduced by PCR mutagenesis. Two types of fragments are amplified from pLenti6-TAg, first by using the pair of primers: 5'-AAGCGGGTTGATAGCCTACA (sense A, SEQ ID NO: 6) and 5'-ATTCAAGCAAAACAGCTGCTAATG (antisense A, SEQ ID NO: 7), and then by using the pair of primers: 5'-CATTAGCAGCTGTTTTGCTTGAAT (sense B, SEQ ID NO: 8) and 5'-TTACAĀATCTGGCCTGCAGT (antisense B, SEQ ID NO: 9). Next, the two fragments are annealed together, and then subjected to amplification using sense A and antisense B primers. The resulting fragment, which has been introduced with the point mutation, is digested with HpaI and PstI, and inserted into the identical site of pLenti6-TAg to construct a temperature-sensitive TAg plasmid (pLenti6-tsTAg).

The complete human telomerase reverse transcriptase isoform 1 (hTERT; Genbank NM_003219; SEQ ID NO: 10) is amplified by PCR from total RNA derived from a colon cancer cell line. The first strand DNA is synthesized using ReverTraAce reverse-transcription system (TOYOBO, Osaka) and 5'-TGACAGGGCTGCTGGTGTCTG (SEQ ID NO: 11), which is a 3'-noncoding primer for hTERT. A cDNA covering the amino-terminal half of hTERT (nucleotide No. 1-2304 of NM_003219) is amplified using 5'-CACCATGC-CGCGCGCTCCCCGCTGCCGA (sense primer; SEQ ID NO: 12) and 5'-GCCTTCTGGACCACGGCATACCGA (antisense primer; SEQ ID NO: 13), while a cDNA covering the carboxyl-terminal half (nucleotide No. 1977-3399 of NM_003219) is amplified using 5'-CACCGGCACTGT-TCAGCGTGCTCAACTACGAG (sense primer; SEQ ID NO: 14) and 5'-TCAGTCCAGGATGGTCTTGAAGTC (antisense primer; SEQ ID NO: 15). Both cDNAs are ligated into pLenti6/V5-D TOPO vector. A Kozak sequence is introduced according to the instruction manual. Then, the fragment from SpeI site, which is located within the vector, to EcoRV site derived from the amino-terminal half is cloned between the same sites in the carboxyl-terminal half to construct the full-length hTERT plasmid (pLenti6-hTERT).

Next, together with helper plasmids (pLP1, pLP2, and pLP/VSVG), pLenti6-tsTAg or pLenti6-hTERT is transfected to almost confluent 293FT cells to produce lentivirus encoding tsTAg (LtV-tsTAg) or hTERT (LtV-hTERT), respectively. After two days of incubation at 37° C., conditioned medium of lentivirus-producing 293FT cells is collected and centrifuged at 3,000 rpm at 4° C. for 15 minutes. The resulting supernatant is transferred into test tubes and stored at −80° C. until use. Fibroblast HT1080 cells are infected with a diluted sample of each lentivirus. The yield of each virus (transformation unit (TU)/ml) can be determined by counting blasticidin (10 µg/ml) resistant colonies.

Immortalization of Human Mesangial Cells $0.5 \times 10^5$ to $1.0 \times 10^5$ primary human mesangial cells are cultured in 6-well plates overnight, and immortalized by infecting the cells at the second passage with 1 ml of viral supernatant containing 6 µg/ml polybrene (Sigma, St Louis, Mo.), in which LtV-tsTAg has been adjusted to $3 \times 10^4$ TU. Stable transfectants are selected by adding 2 µg/ml blasticidin to the culture medium at 32° C. Then, the cells are cloned by limiting dilution to obtain monoclonal cell lines. The cells are further infected with LtV-hTERT ($1 \times 10^4$ TU) during the 11th to 13th passages, and again cloned by limiting dilution. The clones are stored after expansion cell culture. These cell lines are maintained in MCDB-131 medium supplemented with 5% FBS, 2 mM glutamine, 1% penicillin-streptomycin, and 2 µg/ml blasticidin at 32° C. under an atmosphere of 95% air and 5% carbon dioxide.

Selection of Immortalized Human Mesangial Cells

Immortalized human mesangial cells can be selected from clones obtained as described above, by using as indicators: (a) the regulation of tsTAg expression upon temperature shift from 32° C. to 37° C.; (b) the expression of marker proteins at 32° C. and 37° C.; and (c) the TGF-β-responsive expression of PAI-1 or COL4 in culture medium. The specific method is described below.

(1) Response to TGF-β and Detection of Marker Proteins by Western Blotting

Immortalized mesangial cells are cultured at 32° C., and differentiated by culturing them at 37° C. for six days. The stimulation test is conducted by culturing the cells under serum starvation in a medium supplemented with 0.5% FBS and adding TGF-β (R&D Systems, Minneapolis, Minn.) at the concentration indicated in each Example at 32° C. or 37° C. after 24 hours of starvation. The mesangial cells are lysed in 1× Lysis Buffer (Cell Signaling, Beverly, Mass.) containing 1 mM phenylmethanesulfonyl fluoride (Cell Signaling, Beverly, Mass.; hereinafter abbreviated as "PMSF") on ice to extract total protein. The lysate is removed from the culture dish, and treated by sonication using a sonicator (Output 1, TOMY, Tokyo) for five seconds. The sonication product is centrifuged at 15,000 rpm at 4° C. for ten minutes. The protein content in the supernatant is determined using Bradford Protein Assay (Bio-Rad, Hercules, Calif., USA). After reducing proteins in LDS Sample Buffer (Invitrogen, Carlsbad, Calif.) containing 2-mercaptoethanol (hereafter abbreviated as "LDS-2ME"), the resulting sample is stored at −80° C. until use. The cell culture medium is combined with the same buffer, and also stored at −80° C.

Before electrophoresis, the sample is incubated at 70° C. for ten minutes. Then, cell lysates containing an equal amount of total protein, or a same volume of culture liquid are loaded onto a 4-12% NuPAGE Bis-Tris gel (Invitrogen, Carlsbad, Calif.), and electrophoresed using NuPAGE MOPS-SDS Running Buffer (Invitrogen, Carlsbad, Calif.). After electrophoresis, proteins are transferred onto polyvinylidene fluoride (hereafter abbreviated as "PVDF") membrane (Immobilon-P; Millipore, Bedford, Mass.). Then, the membrane is blocked with 5% non-fat dry milk in Tris buffered saline containing 0.1% Tween 20 (hereafter abbreviated as "TBS-T") in a cold room overnight. Next, the prepared membrane is incubated in TBS-T at room temperature for one hour with anti-PAI-1 primary antibody (mouse monoclonal antibody, 1,000 times diluted; Santa Cruz, Santa Cruz, Calif.), anti-COL4 primary antibody (rabbit polyclonal antibody, 5,000 times diluted; Abcam, Cambridge, UK), anti-FN primary antibody (mouse monoclonal antibody, 3,000 times diluted; Sigma, St. Louis, Mo.), anti-SV40 TAg primary antibody (rabbit polyclonal antibody, 2,000 times diluted; Santa Cruz, Santa Cruz, Calif.), hTERT (goat polyclonal antibody, 1,000 times diluted; Santa Cruz, Santa Cruz, Calif.), or anti-β-actin primary antibody (goat polyclonal antibody, 3,000 times diluted; Santa Cruz, Santa Cruz, Calif.). The membranes are washed three times with TBS-T, and further incubated at room temperature for one hour with a horse radish peroxidase- (hereafter abbreviated as "HRP-") conjugated anti-mouse secondary antibody, anti-rabbit secondary antibody (10,000 times diluted, Amersham Bioscience, Little Chalfont Buckinghamshire, UK), or anti-goat secondary antibody (10,000 times diluted, Jackson Immunoresearch, West Grove, Pa.). Next, the membranes are washed, and then the signals are visualized using high-sensitive Chemiluminescence ECL Plus system (Amersham Bioscience, Little Chalfont Buckinghamshire, UK) and Lumijmager (Roche Diagnostics, Penzberg, Germany). Accordingly, it can be tested whether human mesangial cells prepared as described above express T antigen and hTERT, and exhibit the phenotypes of differentiated mesangial cells.

(2) Immunostaining for Marker Proteins

Results obtained by Western blotting as described above can also be confirmed by immunostaining, an alternative test method. Cells of a mesangial cell line, HuVEC cells, and HepG2 cells are cultured in 96- or 24-well cell culture plates, and then tested by immunofluorescence staining. Cells of the immobilized mesangial cell line are cultured at 32° C., and differentiated by culturing them at 37° C. for six days. HepG2 cells and HuVEC are available from American Type Culture Collection (ATCC), and cultured in DMEM supplemented with 10% FBS and 1% penicillin-streptomycin, and in RPMI 1640 supplemented with 10% FBS, 50 μg/ml heparin (Sigma, St Louis, Mo.), and 30 μg/ml endothelial cell growth supplement (hereinafter abbreviated as "ECGS"; BD Bioscience, Bedford, Mass.), respectively. HepG2 cells and HuVEC are cultured at 37° C. under an atmosphere of 95% air and 5% carbon dioxide. After culture, the cells are fixed with methanol-acetone (4:1) at −20° C. for ten minutes. After washing with phosphate buffered saline (hereafter abbreviated as "PBS"), the cells are blocked with PBS containing 10% FBS at 4° C. The fixed cells are incubated in PBS containing 10% FBS with any one of rabbit anti-COL4 antibody (500 times diluted; Abcam, Cambridge, Mass.), mouse anti-FN antibody (500 times diluted; Sigma, St. Louis, Mo.), mouse anti-smooth muscle α actin (hereafter abbreviated as "αSMA") antibody (500 times diluted; Dako, Glostrup, Denmark), rabbit anti-von Willebrand Factor antibody (500 times diluted; Dako, Glostrup, Denmark), mouse anti-cytokeratin 18 antibody (200 times diluted; Chemicon, Temecula, Calif.), and mouse anti-cytokeratin 19 antibody (200 times diluted; Chemicon, Temecula, Calif.). After washing with PBS, the cells are incubated with Alexa 488-labeled anti-rabbit secondary antibody (500 times diluted; Molecular Probes, Eugene, Oreg.) or Cy3-labeled anti-mouse secondary antibody (500 times diluted; Jackson Immunoresearch, West Grove, Pa.). The cells are washed, and then the expression of each marker is tested using fluorescent microscope BZ-8000 (Keyence, Osaka). Clones retaining the mesangial cell phenotype can be obtained based on such assessment results. Clones thus prepared exhibit a growth rate equivalent to that of primary mesangial cell lines, and thus can be cultured continuously over a long period.

Antibodies of the present invention having BMP-neutralizing activity can be used as agents for preventing or treating kidney diseases. The present inventors demonstrated that the production of type IV collagen, which is a mesangial matrix protein, was suppressed by adding a BMP-neutralizing antibody to mesangial cells. The overproduction of mesangial matrix is known to be closely involved in kidney diseases associated with glomerulosclerosis such as diabetic nephropathy. This suggests that kidney diseases can be prevented or treated by administering a BMP-neutralizing antibody. Specifically, neutralizing antibodies against human BMP are expected to be effective in preventing and treating various kidney diseases through suppressing the overproduction of the mesangial matrix.

Herein, kidney disease is defined as a disease associated with a primary or secondary renal disorder. Among various kidney diseases, glomerulonephritis includes focal segmental glomerulosclerosis and diffuse glomerulonephritis (membranous nephritis, proliferative glomerulonephritis, and sclerotic glomerulonephritis). Glomerular disorders accompanying other diseases include lupus nephritis, IgA nephropathy, purpura nephritis, Goodpasture's syndrome, thrombotic microangiopathy, nephrosclerosis (benign and malignant), scleroderma kidney, diabetic nephropathy, renal amyloidosis, Alport's syndrome, HIV nephropathy, and interstitial nephritis.

Furthermore, preferred examples of diseases to which antibodies of the present invention having BMP-neutralizing activity are applicable include glomerulonephritis, lupus nephritis, IgA nephropathy, purpura nephritis, Goodpasture's syndrome, HIV nephropathy, nephrosclerosis (benign and malignant), diabetic nephropathy, and interstitial nephritis; particularly preferred examples include glomerulonephritis, lupus nephritis, IgA nephropathy, nephrosclerosis (benign and malignant), and diabetic nephropathy. In the present invention, however, kidney diseases are not limited to such diseases, but include every disease that meets the definition described above.

The agents of the present invention for preventing or treating kidney diseases contain as an active ingredient an above-described antibody having BMP-neutralizing activity. "Containing as an active ingredient" an antibody having BMP-neutralizing activity means containing as at least one active ingredient an antibody having BMP-neutralizing activity. The content is not limited. Furthermore, the agents of the present invention for preventing or treating kidney diseases may contain other ingredients for enhancing the prevention or treatment of kidney diseases in combination with the antibody having BMP-neutralizing activity.

The BMP-neutralizing antibody of the present invention can be formulated according to standard methods (see, for example, Remington's Pharmaceutical Science, latest edition, Mark Publishing Company, Easton, USA). Further, they may comprise pharmaceutically acceptable carriers and/or additives if necessary. For example, they may contain surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that can be comprised in the agents for preventing or treating kidney diseases of the present invention are not limited to this list. In fact, other commonly used carriers such as light anhydrous silicic acid, lactose, crystalline cellulose, mannitol, starch, carmelose calcium, carmelose sodium, hydroxypropylcellulose, hydroxypropylmethylcellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on, can be appropriately comprised. The compositions may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, BMP-neutralizing antibodies may be dissolved in an isotonic solution comprising, for example, physiological saline, dextrose, and other adjuvants. The adjuvants may include, for example, D-sorbitol, D-mannose, D-mannitol, and sodium chloride. In addition, appropriate solubilizing agents, for example, alcohols (for example, ethanol), polyalcohols (for example, propylene glycols and PEGs), and non-ionic detergents (polysorbate 80 and HCO-50) may be used concomitantly.

If necessary, BMP-neutralizing antibodies may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition" &, Oslo Ed. (1980)). Moreover methods for making sustained-release drugs are known, and these can be applied for BMP-neutralizing antibodies (Langer et al., J. Biomed. Mater. Res. (1981) 15, 167-277; Langer, Chem. Tech. (1982) 12, 98-105; U.S. Pat. No. 3,773,919; European Patent Application (EP) No. 58,481; Sidman et al., Biopolymers (1983) 22, 547-56; EP 133,988).

The agents for preventing or treating kidney diseases of the present invention can be administered either orally or parenterally, but are preferably administered parenterally. Specifically, the agents are administered to patients by injection or drip. The administration methods can be properly selected according to the patient's age and condition. The single-administration dose can be selected, for example, from within the range of 0.0001 to 100 mg of the active ingredient per kg body weight. Alternatively, when the agents are administered to human patients, the dose of the active ingredient can be selected from within the range of 0.001 to 10,000 mg/body. The single-administration dose preferably comprises, for example, BMP-neutralizing antibody at about 0.01 to 2,000 mg/body. However, the dose of an agent for preventing or treating kidney diseases of the present invention is not limited to these examples.

All prior-art documents cited in this specification are incorporated herein by reference.

EXAMPLES

Herein below, the present invention will be specifically described with reference to Examples, but it is not to be construed as being limited thereto.

Example 1

Assay in the Presence of BMP-2 or BMP-4 for the Production of Type IV Collagen in Human Mesangial Cells 1. Cell Culture The human mesangial cell line, clone #130hT-9, was used in this assay. Another patent application previously filed (Japanese Patent Application No. 2006-064802; filing date, Mar. 9, 2006) covers the cell line #130hT-9, which has been deposited under FERM BP-10478 according to the Budapest Treaty.

The cells were cultured in MCDB131 medium (GIBCO) containing 5% fetal bovine serum (FBS) (GIBCO), 10 mM L-glutamine (L-Gln, SIGMA), and 1 vol % Antibiotic-Antimycotic (AA) (GIBCO) at 33° C. under 5% $CO_2$.

The medium was changed with MCDB131 containing 0.5% FBS, 10 mM L-Gln, AA, and 100 µg/ml ascorbic acid (Wako Pure Chemical Industries), and the cells were incubated at a low serum concentration for 24 hours before assays.

2. BMP Treatment

The cells were plated at $1 \times 10^4$ cells/$cm^2$ in 12-well plates (Costar) and incubated at 33° C. Cell adhesion was confirmed, and then the cells were incubated at a low serum concentration in an incubator at 38° C. for 24 hours. Then, the medium was changed with a low serum medium containing 50 ng/ml Recombinant Human Bone Morphogenetic Protein 2 (BMP-2) or Recombinant Human Bone Morphogenetic Protein 4 (BMP-4) (R&D), and 1 µg/ml mouse anti-human BMP-2/4 antibody (R&D, cat# MAB3552). After 72 hours of incubation, the supernatant (CM) was collected.

3. ELISA for Type IV Collagen (ColIV)

100 µl of rabbit anti-ColIV polyclonal antibody (Rockland), which had been diluted to 5 µg/ml with a coating buffer (PIERCE), was added to each well of high-binding 96-well clear plates (Nunc, MaxiSorp). The plates were coated with the antibody at 4° C. overnight. Each well was washed three times with a washing buffer (0.05% Tween20 in PBS), and then 300 µl of a blocking buffer (1% BlockAce (Dainippon Pharmaceutical) in PBS) was added thereto. The plates were blocked at room temperature for two hours or more. After blocking, the plates were washed three times with the washing buffer, and CM collected previously was added thereto. The plates were incubated at room temperature for two hours or more. After two hours, the plates were washed three times with the washing buffer, and 100 µl of mouse monoclonal antibody (CHEMICON) diluted with the blocking buffer to 1 µg/ml was added thereto. The plates were allowed to stand at room temperature for two hours. After washing the plates three times with the washing buffer, AP-conjugated anti-mouse antibody (Zymed) 1,000 times diluted with the blocking buffer was added, and the plates were incubated at room temperature for one hour. After one hour, the plates were washed three times with the washing buffer. 100 µl of a solution prepared using p-Nitrophenyl Phosphate Tablet Sets (SIGMA) according to the appended protocol was added to each well. The plates were shaken in the dark at room temperature for 20 to 90 minutes. The absorbance at 405 nm was measured over time in WALLEC ARBO-HTS Multilabel counter (Perkin Elmer). The contents of ColIV in the supernatants were estimated based on the determined absorbance. The result is shown in FIG. 1. The cells cultured in the presence of BMP-2 or BMP-4 produced ColIV at a high concentration. The production was significantly suppressed by adding the anti-BMP2/4 antibody.

Example 2

Preparation of Anti-Human BMP-4 Antibody and Assessment of the Antibody for its Drug Efficacy 1. Preparation of Hybridoma Producing Anti-Human BMP-4 Antibody
(1) Preparation of Hybridomas Two MRL-1pr/1pr mice (female; starting immunization at six weeks of age; Japan Charles River) were immunized with human BMP-4 (R&D Laboratories) by the procedure described below. 50 µg/head of the antigen was used for the first immunization. The antigen was emulsified using Freund's complete adjuvant (FCA), and injected subcutaneously into the mice. After two weeks, 50 µg/head of the antigen emulsified using Freund's incomplete adjuvant (FIA) was injected subcutaneously into the mice. Then, boosters were carried out three times in total at one-week intervals. After the titer of antibody to the antigen was confirmed to be elevated in sera by ELISA described below in (3), the final immunization was carried out by intravenously injecting the mice with antigen diluted by PBS(−) (10 µg/head). Three days after the final immunization, P3U1 and mouse spleen cells were fused together by a conventional method using PEG1500. Fused cells, namely hybridomas, were cultured in RPMI1640 supplemented with 10% FBS.

(2) Selection of Hybridomas

On the next day of fusion, the fused cells were suspended in semisolid medium (StemCells), and underwent hybridoma selective culture and colony formation.

Nine or ten days after fusion, hybridoma colonies were isolated and plated in 96-well plates containing the HAT selection medium (RPMI1640 supplemented with 10% FBS, 2 vol % of HAT 50× concentrate (Dainippon Pharmaceutical), and 5 vol % of BM-Condimed H1 (Roche Diagnostics)) such that each well contained cells of one colony. After three to four days of culture, the culture supernatant was collected from each well, and hybridomas were selected based on the human BMP-4-binding activity determined by ELISA described below in (3).

As a result, clones BF1009 and BF1066 producing antibodies that bound to human BMP-4 were obtained.

Isotyping of each monoclonal antibody was carried out using mouse monoclonal antibody isotyping kit Iso Strip™ (Roche Diagnostics; 1 493 027). The isotype of monoclonal antibody produced by hybridoma BF 1009 was IgG2b for the heavy chain and κ for the light chain. The isotype of monoclonal antibody produced by hybridoma BF 1066 was IgG1 for the heavy chain and κ for the light chain.

(3) ELISA

Human BMP-4 was diluted to 0.1 to 0.5 μg/ml with coating buffer (0.1 M $NaHCO_3$ (pH 9.6), 0.02% $NaN_3$), and 100 μl of the solution was added to each well of immunoplates. The plates were coated by incubating them at 4° C. overnight or for a longer period. The supernatants were discarded, or each well was washed three times with 300 μl of rinse buffer (0.05% Tween 20, PBS-) using a plate washer, and then 200 μl of diluent buffer (Blocking One, Nacalai Tesque) was added to each well. The plates were blocked by incubating them at room temperature for two hours or more, or at 4° C. overnight. The supernatants were discarded. Sera, culture supernatants, purified antibodies, or such were appropriately diluted with diluent buffer, and a 100-μl aliquot was added to each well. The plates were incubated at room temperature for one hour, and then each well was washed three times with 300 μl of rinse buffer using a plate washer. Then, peroxidase-labeled goat anti-mouse Fab antibody was 1,000 to 5,000 times diluted with diluent buffer, and a 100-μl aliquot was added to each well. The plates were incubated at room temperature for one hour. Each well of the plates was washed five times with 300 μl of rinse buffer using a plate washer. After 100 μl of peroxidase substrate (Kirkegaad & Perry Laboratories) was added to each well, color development was carried out at room temperature for 10 to 60 minutes. 100 μl of a stop solution (Kirkegaad & Perry Laboratories) was added to each well to terminate the color development. Colorimetric determination was carried out by measuring absorbance at 405 nm using an absorption spectrometer.

2. Purification of Antibody from Hybridoma Culture Supernatant

The hybridomas prepared as described above were cultured in roller bottles containing Hybridoma-SFM (Invitrogen). The culture supernatants were separated from the cells by centrifugation. After a Protein G Sepharose Fast Flow column (Amersham) was washed with an equilibration/adsorption buffer (0.15 M NaCl/PBS(−)), culture supernatant was loaded onto it. Again, the column was washed with the equilibration/adsorption buffer. The antibody was eluted with an elution buffer (100 mM glycine-HCl (pH 2.7)). Immediately, the eluate was neutralized with a neutralization buffer (2 M Tris-HCl (pH 9.0)). The purified antibody was concentrated and simultaneously the buffer was changed with PBS (−) by ultrafiltration. The antibody was sterilized using 0.22-μm sterile filter (Millipore).

3. Antibody Screening

Antibodies were screened by reporter gene assay using a BMP responsive element and matrix production assay using immortalized human mesangial cells.

By reporter gene assay using a BMP responsive element, antibodies having BMP-4-neutralizing activity were selected from BMP-4-binding antibodies obtained from the hybridomas described above. Specifically, HepG2 cells were plated at $1×10^5$ cells/ml in 96-well plates, and incubated at 37° C. under 5% $CO_2$ overnight. Then, 100 ng of the reporter gene (pGL3-BRE) and 1 ng of the control gene (pRL-SV40; Promega) were introduced using Lipofectamine-2000 (Invitrogen) according to the appended protocol. After gene transfer, the cells were incubated at 37° C. under 5% $CO_2$ overnight, 10 ng/ml BMP-4 and a 1/10 volume of hybridoma culture supernatant were added thereto. The cells were further incubated overnight. After overnight incubation, the activity of reporter gene luciferase was determined using Dual-Luciferase Reporter Assay System (Promega) according to the appended protocol. ARVO HTS 1420 Multilabel Counter was used to detect chemiluminescence.

Clones having the neutralizing activity were tested for their cross-reactivity to rat BMP-4 by ELISA using a peptide expressed as a GST fusion with the N terminal peptide whose sequence is different between rat and human. Specifically, the rat or human gene encoding the N terminal peptide was amplified by PCR using rat or human BMP-4 as a template, respectively. The templates were prepared by PCR cloning from commercially available cDNA libraries. The sequences of primers used are shown in SEQ ID NOs: 26 and 27 for rat and SEQ ID NOs: 28 and 29 for human.

```
                                              SEQ ID NO: 26/
5'-GGGATCCCCAGTCCCAAGCATCACCCACAG-3'

SEQ ID NO: 27/
5'-CTCGAGTTAGTTCTTATTCTTCTTCCTGGA-3'

SEQ ID NO: 28/
5'-GGGATCCCCCAAGCCAAACACAAACAGCGG-3'

SEQ ID NO: 29/
5'-CTCGAGTTAGCTGGACTTAAGGCGTTTCCG-3'
```

The amplified PCR products were digested with restriction enzymes BamHI and XhoI, and inserted into pGEX5X-2 (Amersham-Pharmacia) predigested with the same enzymes. After the yielded plasmids were sequenced using a DNA sequencer, E. coli DH5α was transformed with the plasmids. GST fusions with the N terminal peptide were prepared using the transformed E. coli cells. The E. coli cells were cultured in LB-Amp up to mid-log phase by a conventional method, and then IPTG was added at the final concentration of 1 mM to induce protein expression. After two hours of culture following the addition of IPTG, the E. coli cells were collected by centrifugation. The collected E. coli cells were lysed using Bug Buster Protein Extraction Reagent (Novagen) to collect the expressed proteins. GST fusion peptides were purified from the collected proteins using a glutathione column.

The purified GST fusion peptides were diluted to 1 μg/ml. A 100-μl aliquot was added to each well of immunoplates. The plates were allowed to stand at room temperature for one hour to immobilize the peptides onto the plates. After blocking with 3% BSA in PBS, each of 1 μg/ml antibody solutions was added thereto. The plates were allowed to stand at room temperature for one hour. After washing with PBS containing 0.05% Tween20, 5,000 times-diluted HRP-anti mouse IgG (Zymed) was added thereto. The plates were allowed to stand for another one hour at room temperature. After washing with PBS containing 0.05% Tween20, TMB solution was added to assess the reactivity. Antibodies BF1009 and BF1066 were selected because they bound to both rat and human BMP-4 peptides.

Using the method described above, these two antibodies were demonstrated to have the activity of suppressing matrix production in immortalized mesangial cells.

4. Assessment of Drug Efficacy of Anti-BMP Antibody in Unilaterally Nephrectomized Thy1 Nephritis Model (1) Preparation of Unilaterally Nephrectomized Thy1 Nephritis Model The unilaterally nephrectomized Thy1 nephritis model is a model for chronic glomerulonephritis involving the pathological condition of mesangial proliferative nephritis, leading to loss of kidney function via glomerulosclerosis, tubulointerstitial disorder, and others.

The nephritis model was prepared by excising left kidneys from seven-week-old rats (Slc: Wistar, male) and administering anti-Thy1 antibody (Anti-Rat CD90 (Thy1.1) Monoclonal Antibody-Ascites (Cedarlane, Code No. CL005A)) at 1 mg/kg into the caudal veins.

(2) Assessment of Drug Efficacy of Anti-BMP Antibody

Figure 2:
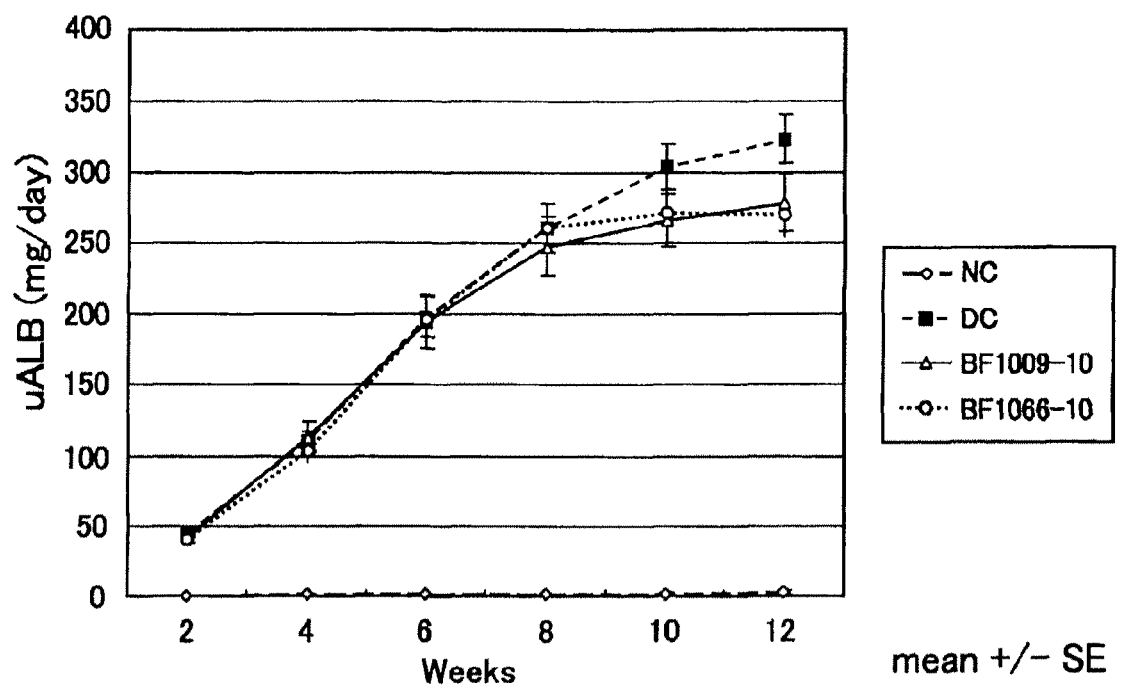
FIG. 2 is a graph showing the drug efficacy of anti-human BMP antibodies in a kidney disease. The level of excreted urinary albumin in chronic glomerulonephritis model rats was reduced when the antibody produced by hybridoma BF1009 or BF1066 was administered to the rats.

Two weeks after preparation of the model, either anti-BMP antibody BF1009 or BF1066 was administered to 15 rats from the caudal vein at either the dose of 1 mg/kg or 10 mg/kg. The antibody was administered at the frequency of once every two weeks in the period of first ten weeks after the start of administration, and then once a week. To collect 24-hour urine, the rats were transferred to metabolic cages once every two weeks after the start of administration. The contents of albumin in the collected urine samples were determined using Hitachi 7170 Autoanalyzer, and normalized by the urine volume to calculate the amount of albumin excreted into 24-hour urine. The time courses of control ("NC"), disease control ("DC"), and groups administered with anti-BMP antibody at 10 mg/kg ("BF1009-10" and "BF1066-10") are shown in FIG. 2.

The result shows that the contents of urinary albumin eight weeks after the start of antibody administration were different between each antibody administration group and control group. This suggests that anti-BMP antibodies are effective for kidney diseases. Furthermore, the difference in the content of urinary albumin between each antibody administration group and control group became larger after 12 weeks, suggesting that much greater drug efficacy is achieved by shortening the administration interval.

INDUSTRIAL APPLICABILITY

The present invention provides novel agents for preventing and treating kidney diseases. Drug therapy for kidney diseases includes symptomatic therapy using antihypertensive agents (ACE inhibitors, angiotensin II receptor antagonists, and Cα antagonists), diuretic agents (thiazides and loop diuretic agents), etc. However, these treatments do not directly prevent kidney damage. Furthermore, steroidal therapy is inapplicable to diabetic nephropathy. The therapeutic agents of the present invention for kidney diseases including diabetic nephropathy are based on a mechanism that is completely different from that of previous therapeutic agents, and thus can provide new therapeutic options for kidney disease patients.

The invention claimed is:

1. A hybridoma deposited under accession number FERM ABP-10873 or accession number FERM ABP-10874.

2. A hybridoma deposited under accession number FERM ABP-10875 or accession number FERM ABP-10876.

3. An anti-human BMP-4 antibody produced by a hybridoma deposited under accession number FERM ABP-10873 or accession number FERM ABP-10874.

4. A method for treating a kidney disease, which comprises administering an antibody having BMP-neutralizing activity, or an antigen-binding fragment thereof, to a patient in need of treatment of the kidney disease, wherein the kidney disease is selected from the group consisting of: diabetic nephropathy, chronic glomerulonephritis, lupus nephritis, interstitial nephritis, benign nephrosclerosis, and malignant nephrosclerosis, and wherein the BMP is BMP-2 or BMP-4.

5. An anti-human BMP-4 antibody produced by a hybridoma deposited under accession number FERM ABP-10875 or accession number FERM ABP-10876.

6. The method of claim 4, wherein the BMP is a human BMP.

7. The method of claim 4, wherein the BMP is BMP-4.

8. The method of claim 4, wherein the antibody is a monoclonal antibody.

9. The method of claim 4, wherein the antibody is a recombinant antibody.

10. The method of claim 4, wherein the antibody is a chimeric antibody, humanized antibody, or human antibody.

11. The method of claim 4, wherein the kidney disease is diabetic nephropathy.

12. The method of claim 4, wherein the antibody is selected from the group consisting of: an antibody produced by a hybridoma deposited under accession number FERM ABP-10873, an antibody produced by a hybridoma deposited under accession number FERM ABP-10874, an antibody produced by a hybridoma deposited under accession number FERM ABP-10875, and an antibody produced by a hybridoma deposited under accession number FERM ABP-10876.

13. The method of claim 12, wherein the antibody is the antibody produced by the hybridoma deposited under accession number FERM ABP-10873 or the hybridoma deposited under accession number FERM ABP-10874.

14. The method of claim 12, wherein the antibody is the antibody produced by the hybridoma deposited under accession number FERM ABP-10875 or the hybridoma deposited under accession number FERM ABP-10876.

* * * * *